United States Patent
Papadopoulos et al.

(10) Patent No.: US 8,216,798 B2
(45) Date of Patent: *Jul. 10, 2012

(54) PERIPHERAL-TYPE BENZODIAZEPINE RECEPTOR EXPRESSION LEVEL AS AN INDEX OF ORGAN DAMAGE AND REGENERATION

(75) Inventors: Vassilios Papadopoulos, North Potomac, MD (US); Thierry Hauet, Saint Benoit (FR)

(73) Assignee: Georgetown University, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/896,522

(22) Filed: Oct. 1, 2010

(65) Prior Publication Data
US 2011/0081295 A1    Apr. 7, 2011

Related U.S. Application Data

(62) Division of application No. 12/569,511, filed on Sep. 29, 2009, now Pat. No. 7,863,010, which is a division of application No. 10/512,060, filed as application No. PCT/US03/12385 on Apr. 22, 2003, now Pat. No. 7,615,355.

(60) Provisional application No. 60/374,136, filed on Apr. 22, 2002.

(51) Int. Cl.
*G01N 33/53* (2006.01)

(52) U.S. Cl. ........................................... 435/7.2
(58) Field of Classification Search .................. None
See application file for complete search history.

(56) References Cited

U.S. PATENT DOCUMENTS 7,615,355 B2 * 11/2009 Papadopoulos et al. ....... 435/7.1
7,863,010 B2 *  1/2011 Papadopoulos et al. ....... 435/7.2

OTHER PUBLICATIONS

Hauet et al. (2002) Transplantation 74: 1507-1515.*

* cited by examiner

*Primary Examiner* — Michael Pak
(74) *Attorney, Agent, or Firm* — Buchanan Ingersoll & Rooney

(57) ABSTRACT

The present invention relates to methods, reagents, and kits for assessing organ damage, such as damage due to ischemia reperfusion injury, in the course of a transplantation therapy and/or for assessing organ regeneration following transplantation therapy. The invention provides a method for determining an index of organ health in the course of transplantation therapy comprising measuring the expression level of peripheral-type benzodiazepine receptor (PBR) in the organ. Measuring the expression level of PBR is also useful for assessing the progress of organ regeneration in the course of transplantation therapy by comparing the index of organ health. The expression level of PBR may be used as a predictor of the outcome of transplantation therapy.

1 Claim, 13 Drawing Sheets

PERIPHERAL-TYPE BENZODIAZEPINE RECEPTOR EXPRESSION LEVEL AS AN INDEX OF ORGAN DAMAGE AND REGENERATION

CROSS-REFERENCE TO EARLIER APPLICATIONS

This application is a divisional of U.S. patent application Ser. No. 10/512,060, filed Dec. 8, 2005, now allowed, which is a U.S. National Stage of PCT/US 2003/12385, filed Apr. 22, 2003, which claims the benefit of U.S. Provisional Application No. 60/374,136, filed Apr. 22, 2002, each earlier application is hereby expressly incorporated by reference in its entirety and is assigned to the assignee hereof.

GOVERNMENT FUNDING

Work described herein was supported in part by funding from the National Institute of Health. The United States Government may have certain rights in the invention.

BACKGROUND OF THE INVENTION

1. Field of the Invention

The present invention relates to methods, reagents, and kits for assessing organ damage, such as damage due to ischemia reperfusion injury, in the course of a transplantation therapy and/or for assessing organ regeneration following transplantation therapy.

2. Description of the Related Art

The central focus of organ transplantation therapy has been the prevention of acute rejection. (See for example, *The Handbook of Transplantation Management* by Leonard Makowka, CRC Press, 1991.) In attempting to prevent acute rejection, therapies have evolved to reduce or to control the appropriate recognition of allopeptides by helper T cells. As a result, early rates of acute rejection have lowered to below 20% and increased one-year renal allograft survival to well above 80%. Unfortunately, this improved early graft survival has not translated to improved long-term graft survival. Graft half-life and the effects of chronic allograft nephropathy have remained relatively constant throughout the eras of calcineurine inhibition and monoclonal antibody therapies.

Survival of any organ or cell is dependent on the availability of oxygen and crucial nutrients and removal of cellular waste. Metabolic processes must function in a balanced manner to maintain cellular homeostasis. Disruption of this critical balance by physical, chemical or oxidative stress results in changed rates and direction of normal biochemical and molecular reactions as the cells attempt to maintain cell functions and adapt to stressful conditions.

Oxidative stress is induced by the total stoppage of blood flow (ischemia) incident to the removal of an organ from a donor, cold storage, warming, and re-implantation into a recipient in the course of transplantation and results in a fundamental metabolic imbalance. Switching from aerobic to anaerobic conditions results in an accumulation of harmful substrates and stimulation of catabolic pathways to eliminate undesirable metabolic byproducts. This metabolic imbalance continues as long as a lack of oxygen lasts. Ultimately, diminished metabolic rates, metabolic acidosis and calcium and sodium overloading accelerate cell and organ death. Reperfusion, resumption of oxygenated blood flow to an ischemic organ, intensifies injury by providing conditions that activate free radical production and a cascade of reactions leading to recruitment and activation of neutrophils and platelets. Organ damage caused in this process is known as ischemia reperfusion injury (IRI).

With respect to kidney transplant, it is known that cold storage may cause delayed graft function (DGF), which in turn causes reduced short and long term renal allograft survival (Ojo, et al., *Transplantation*, 63:968-974, 1997). However, while prolonged cold ischemia is known to have detrimental effects on graft survival, the cellular and molecular responses of the kidney to ischemic insult are not completely understood. Various experimental studies have tried to determine the mechanisms involved in acute ischemic renal failure. (See, for example, a review by Sheridan and Bonventre (*Curr. Opin. Nephrol. Hypertension*, 9:427-34, 2000).

Its remarkable regeneration potential enables the kidney to completely restore its function and to replace damaged cells and to restore epithelial continuity. However, in different situations, recovery is delayed or does not occur at all. The mechanism underlying the detrimental effect of cold ischemia and thermal injury on graft survival remains unclear and the factors that trigger and control the repair process are poorly understood. For background on kidney disease including theory and practice known to one of skill in the art, see *Disease of the Kidneys* ($6^{th}$ Ed.) by Robert Schrier and Carl Gottschalk, Little Brown and Company (1996).

Currently, assessment of renal graft dysfunction following transplantation relies on the measurement of plasma creatinine and the often inconclusive histological results of a renal biopsy. In addition, the results of such measurements are essentially descriptive and are not effective predictive markers.

Therefore, the art is in need of improved methods for the assessment of organ health in the course of transplantation therapy, for outcome prediction, and for the assessment of regeneration following transplantation therapy. These and other objects are provided by the present invention.

SUMMARY OF THE INVENTION

The invention provides a method for determining an index of organ health in the course of transplantation therapy comprising measuring the expression level of peripheral-type benzodiazepine receptor (PBR) in said organ whereby said index is determined.

The invention also provides for the method further comprising obtaining a tissue sample of the organ.

The invention further provides for the method wherein the organ is selected from among one or more of kidney, heart, lung, cornea, skin, liver, bone marrow, vascular graft, pancreas, and small bowel.

The invention further provides for the method wherein the organ is a kidney.

The invention further provides for the method wherein the index of health is an index of ischemia reperfusion injury.

The invention further provides for the method wherein the index of organ health is an index of ischemia reperfusion injury incident to a renal transplant procedure.

The invention further provides for the method wherein the expression level of peripheral-type benzodiazepine receptor is measured using a method chosen from one or more of immunohistochemistry, electrophoretic blotting, hybridization of a nucleic acid probe to mRNA, observing binding of radiolabeled ligand, observing binding of fluorescence labeled ligand, observing binding of isotopically labeled ligand, and in vivo scanning using isotopically labeled ligand of PBR.

The invention further provides for the method wherein the index of organ health is determined at one or more points in the course of transplantation therapy selected from among the time of organ extraction, the time of organ storage, immediately prior to organ implantation, following reperfusion in the recipient, and at one or more intervals following the transplantation procedure.

The invention further provides a method for assessing the progress of organ regeneration in the course of transplantation therapy by comparing the index of organ health, determined according to a method set forth above, to normalized data of the index of organ health.

The invention further provides a method of predicting the outcome of transplantation therapy wherein the index of organ health is determined by the method set forth above and comprising the step of comparing said index with a correlation between said index and previous outcomes whereby a likely outcome is predicted.

The invention further provides a method of assessing transplant therapy procedures comprising determining an index of organ health according to a method set forth above and comparing index measurements as a function of parameters of said transplant therapy procedures.

The invention further provides a kit of materials and/or reagent(s) for the practice of the method of the invention.

The invention further provides such a kit of materials and/or reagent(s) for the practice of the method of the invention comprising an indicator of PBR expression selected from among an antibody to PBR, a nucleic acid probe capable of specific hybridization to mRNA encoding PBR, and a radiolabeled, isotopically labeled, or fluorescence labeled ligand of PBR.

The invention further provides such a kit of materials and/or reagent(s) for the practice of the method of the invention further comprising control and or comparative samples.

The invention further provides a kit of materials and reagent(s) for the practice of the method of the invention comprising a microanalytical apparatus.

The invention further provides such a kit wherein the microanalytical apparatus is a lab-on-a-chip.

The invention further provides a method for treating a patient in the course of transplantation therapy comprising administration of an effective amount of a pharmaceutical composition comprising an agent which modulates expression of PBR.

The invention further provides a method for treating a patient in the course of transplantation therapy comprising administration of an effective amount of a pharmaceutical composition comprising an agent which modulates the activity of PBR.

The invention further provides for such methods of treatment wherein the progress of the treatment is monitored by measuring the index of organ health according to a method set forth above.

BRIEF DESCRIPTION OF THE DRAWINGS

The objects and advantages of the invention will become apparent from the following detailed description of the preferred embodiments thereof in connection with the accompanying drawings, in which.

DETAILED DESCRIPTION OF THE PREFERRED EMBODIMENTS OF THE INVENTION

Figure 1A:
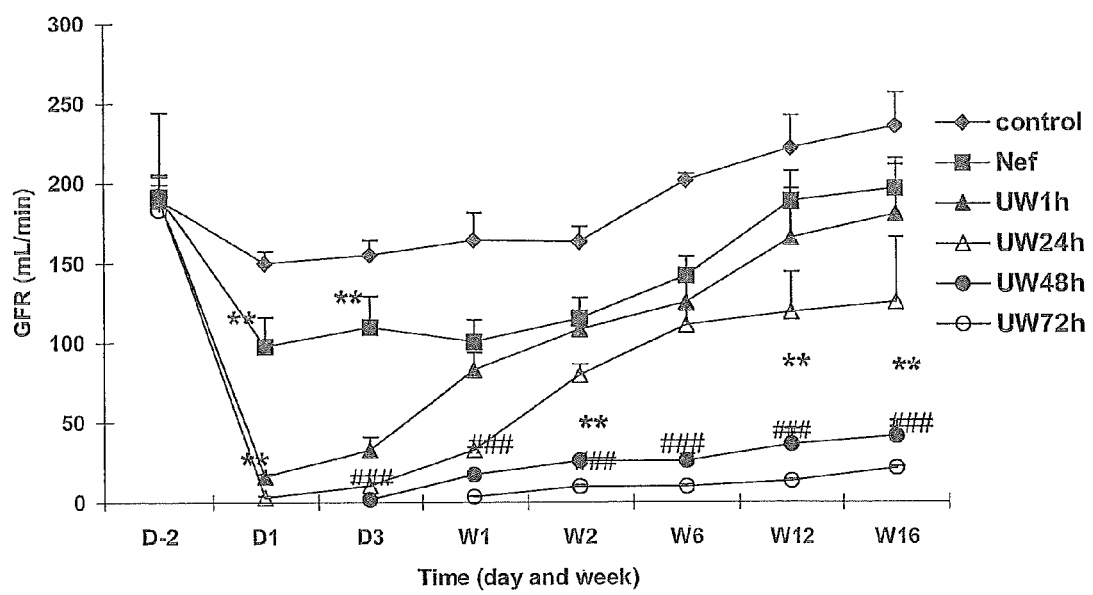
FIG. 1 shows the effect of cold ischemia on the glomerular filtration rate (GFR) (A), sodium reabsorption (B), proteinuria (C) and alanine excretion (D). Renal function was determined in control and uninephrectomized animals (Nef) (control, closed diamond and Nef, closed square). Autotransplanted kidneys were cold-flushed and preserved with University of Wisconsin (UW) solution for 1 h (UW1 h, closed triangle), 24 h (UW24 h, open square), 48 h (UW48 h, open circle) and 72 h (UW72 h, closed circle). (*$P<0.05$ UW1 h and UW24 h vs. Control and Nef, $P<0.01$ UW1 h and UW24 h vs. Control and Nef, *$P<0.001$ UW1 h and UW24 h vs. Control and Nef, #$P<0.05$ UW48 h and UW72 h vs. Control and Nef, ##$P<0.01$ UW48 h and UW72 h vs. Control and Nef, ###$P<0.001$ UW48 h and UW72 h vs. Control and Nef).

The present invention provides for the determination of an index of organ health, damage and/or viability by measuring the expression of peripheral-type benzodiazepine receptor (PBR). The method is particularly useful for assessment or outcome prediction in the course of transplantation therapy.

The method is preferably used to determine an index of organ health after ischemia and reperfusion in the course of organ transplantation therapy.

The invention is based on the discovery of the inventors that PBR expression is correlated with ischemia reperfusion injury and recovery, and that the expression level of PBR tracks known injury parameters. Therefore, measurement of the expression level of PBR in the course of transplantation therapy and/or subsequent to a transplant procedure provides a basis for a method of assessing organ health, damage, recovery, and predicting the outcome of such therapy.

The determination of PBR expression levels according to the invention may also be utilized as part of a research method for the development of transplantation strategies and techniques. In this aspect of the invention, variations in transplantation strategies and techniques may be assessed by tracking the index of organ health, damage and/or viability by measuring the expression of peripheral-type benzodiazepine receptor (PBR).

Furthermore, the discovery forms a basis of a method of treatment wherein agents which modulate PBR expression or activity is administered to improve organ regeneration following a transplant procedure or other ischemic occurrence. In this aspect of the invention, a therapeutically effective amount of an agent which modulates PBR expression or activity is administered to a patient in need of treatment. Such a patient would typically be recovering from transplantation therapy, preferably renal transplantation therapy, although the method may be applied to a patient having experienced another cause of ischemic damage.

Reagents and materials for the determination of PBR expression levels may be conveniently packaged as a kit for the practice of the methods of the invention. Such kits preferably comprise a reagent useful for the measurement of PBR expression levels and optionally additional materials, such as slides and fixing material, precast gels, secondary antibodies, apparatus parts for use in the method, and the like. Preferably, such a kit of materials and/or reagent(s) for the practice of the method of the invention comprises an indicator of PBR expression selected from among an antibody to PBR, a nucleic acid probe capable of specific hybridization to mRNA encoding PBR, and a radiolabeled, isotopically labeled, or fluorescence labeled ligand of PBR. Such a kit of materials and/or reagent(s) may also comprise control and/or comparative samples. In one embodiment of the invention, a kit of materials and reagent(s) for the practice of the method of the invention comprises a microanalytical apparatus, for example, the microanalytical apparatus may be in the form of a lab-on-a-chip apparatus. In an alternative embodiment, the kit may be supplied as a lab-on-a-chip apparatus for use in an automated analysis system.

Mitochondria are hypothesized to play a central role in ischemia reperfusion injury because the switch of aerobic to anaerobic conditions is one of the first steps in the ischemic process. At present, there is no specific marker to assess mitochondrial function, viability and recovery. Previous studies have evaluated different techniques such as nuclear magnetic resonance spectroscopy. See, for example, a review by Neild et al., (*Nephrol. Dial. Transplant.*, 12:404-17, 1997). However, this technique is generally too expensive and impractical for routine use.

Cholesterol is a critical component of plasma membranes. Molitoris et al., have suggested that renal ischemia may cause an acute reduction in apical membrane cholesterol, relative to its total phospholipid content (Molitoris et al., *J Membr. Biol.*, 106:233-242, 1998). Recently, Zager et al., have determined that in vivo IRI acutely increased cholesterol ester (CE), but not free cholesterol (FC), content, indicating perturbed CE/FC cycling (Zager et al., *Kidney Int.*, 59:1750-61, 2001). Other studies have demonstrated that when cholesterol levels are decreased in cultured proximal tubular cells, tubule susceptibility to injury is markedly enhanced (Zager et al., *Kidney Int.*, 56:1788-97, 1999). The biochemical modification of plasma membrane cholesterol either by cholesterol esterase or cholesterol oxidase treatment, in cultured proximal tubular cells, is rendered highly vulnerable to superimposed hypoxic or toxic challenges (Zager et al., supra). Exposition of proximal tubular segments to high doses of cholesterol esterase or cholesterol oxidase induced profound mitochondrial dysfunction followed by necrotic cell death (Zager et al., *Kidney Int.*, 58:193-205, 2000). A correlation between elevated cholesterol and cytoresistance by 18 to 24 hours after different forms of in vivo renal injury was also demonstrated and correlated to proximal tubular cell resistance to superimposed attack (Zager et al., *Kidney Int.*, 56:1788-97, 1999; Zager et al., *Am. J. Pathol.*, 157:1007-16, 2000; Zager et al., *Am. J. Pathol.*, 159:743-52, 2001).

PBR is an 18-kDa protein which was originally discovered because it binds the benzodiazepine diazepam with relatively high affinity (Papadopoulos *Endocr. Rev.*, 14:222-240, 1993). PBR is an indispensable element of the cholesterol transport machinery (Papadopoulos, *Proceedings of the Society for Experimental Biology & Medicine*, 1998; 217:130-142). This is consistent with data showing that PBR is a high affinity cholesterol binding protein. (H. Li et al., *Proceedings of the National Academy of Sciences USA*, 98:1267-1272, 2001; J. J. Lacapere et al., *Biochem Biophys Res Com.*, 284:536-641, 2001). PBR is mainly localized in the outer mitochondrial membrane and was initially described as a functional component of the steroidogenic machinery mediating cholesterol delivery from the outer to the inner mitochondrial membranes (Anholt et al., *J. Biol. Chem.*, 261:576-83, 1986; Papadopoulos, et al., *J. Biol. Chem.*, 265:3772-79, 1990). However, PBR is present in most tissues examined including kidney. The functional mitochondrial PBR is a multimeric receptor complex. It is composed of at least the 18-kDa isoquinoline binding protein organized in clusters of four to six molecules, the 34-kDa voltage-dependent anion channel, and the adenine nucleotide carrier (Garnier et al., *Mol. Pharmacol.*, 45:201-211, 1994). Further studies have demonstrated that targeted disruption of the PBR gene in Leydig cells resulted in the arrest of cholesterol transport into mitochondria and transfection of the PBR-disrupted cells with a PBR cDNA rescued cholesterol transport (Papadopoulos et al., *J. Biol. Chem.*, 272:32129-35, 1997). From these studies a region of the cytosolic carboxyl terminus receptor was identified as a cholesterol-binding site (Li et al., *Proc. Natl. Acad. Sci. USA*, 98:1267-72, 2001).

Because cholesterol is a major component of plasma membrane, we hypothesized that PBR could be involved in renal reparation after cold ischemia and reperfusion in an autotransplanted pig kidney model. There is growing evidence of the importance of PBR in the transport of the substrate cholesterol into mitochondria in streroidogenic (Krueger et al., *J. Biol. Chem.*, 265:15015-22, 1990) and liver tissues (Tsankova et al., *Eur. J. Pharm.*, 294:601-7, 1995). We used a well-established autotransplant pig kidney model and we have focused on the renal function and morphology and PBR expression.

In a model study, described in the Examples below, PBR levels were greater in kidneys preserved at 4° C. in University of Wisconsin (UW) solution for 1 h and 24 h compared to kidneys preserved for 48 h and 72 h. Interestingly, PBR immunoreactivity was associated with the less severe urine excretion of TMAO. One week after surgery, PBR levels recovered in kidneys where reparation was most efficient (1 h and 24 h). However, after week four, the intensity of the staining decreased in the 24 h group and to a greater extent in the 1 h groups. The data disclosed herein is consistent with a study suggesting that PBR might be involved in nerve degeneration and regeneration (Lacor et al., *Brain Res.*, 815:70-80, 1999).

A significant result of the present study is the observation that cold ischemia and particularly long preservation time (i.e., 24 to 72 hours) induced greater functional deterioration when compared with shorter cold ischemia times such as about 1 hour. In model experiments, $Na^+$ and aminoaciduria transport was dramatically impaired after cold preservation particularly after 72 h of cold ischemia. These functional results were related to observed differences in tubular cells, which were damaged in 48 hour and 72 hour groups when compared to 1 hour and 24 hour preserved groups.

Previous studies have demonstrated that natriuresis occurs as a result of IRI, which involves a pronounced down-regulation of different $Na^+$ transporters and a loss of $Na^+$—$K^+$-ATPase pump distribution from basal to inappropriate apical location (Breton et al., *J. Am. Soc. Nephrol.*, 9:155-66, 1998; Alejandro et al., *Kidney Int.*, 48:1308-15, 1995; Wang et al., *J. Am. Soc. Nephrol.*, 9:605-13, 1998; Kwon et al., *Kidney Int.*, 55:963-75, 1999). Reductions in glomerular filtration rate (GFR) have been attributed to persistent vasoconstriction, activation of tubuloglomerulo feedback as a result of a high $Na^+$ and solute delivery to the macula densa, and an increase in paracellular permeability resulting in "back-leak" of glomerular filtrate (Trocha et al., *Ann. Surg.*, 230:105-13, 1999). The development of significant and progressive proteinuria is also related to chronic injury and extensive fibrosis where glomeruli were mostly obsolescent with focal segmental collapse of the capillary loops and were associated with the diffuse infiltration of interstitial mononuclear cells. Thus, renal medulla injury is associated with the time duration of cold ischemia as demonstrated by the osmolite excretion in urine.

The expression level of PBR may be observed by any means recognized in the art including both in vivo and ex vivo methods. As an example, a preferred method is immunohistochemical staining and microscopic observation of tissue samples. Using immunohistochemistry to observe PBR expression in a pig model of IRI recovery in the course of renal transplant, it is observed that PBR staining density increases after IRI. Once reparation was complete, PBR staining tends to drop again, but the staining is still detected in more than 90% of tubular sections. By contrast, when regeneration was incomplete or slowed, PBR expression remains intense but limited to few tubular sections. A lack of PBR staining as observed by immunohistochemistry is an indicator of more severe organ damage and/or a predictor of organ failure. PBR was not detected in interstitial fibrosis and necrotic tissue, such as in non primary function, i.e., where an organ does not function following transplantation. Therefore, the level and course of PBR expression in organ tissues can be used to assess organ health as well as the progress of recovery from organ damage, such as organ damage caused by IRI. These results indicate that measurements of PBR expression may also be used as an indicator of organ viability.

These conclusions are supported by further observations such as the correlation with citrate excretion. The formation of citrate from acetyl coenzyme A and oxaloacetate is catalyzed by citrate synthase, which is a key enzyme in the tricarboxylic acid cycle (Ullian et al., *Hypertension*, 35:875-79, 2000). Citrate synthase activity is also related to the mitochondrial membrane integrity. In the model of IRI in renal transplant, in prolonged conservation groups, an observed reduction of urinary citrate excretion is consistent with reduced renal parenchymal citrate synthase activity and loss of mitochondrial membrane integrity during the first weeks. Citrate excretion increased in these groups after week two, correlated with reparation progress. However, citrate excretion remained at a low rate when compared to the other groups. Consequently, we observe that citrate excretion is consistent with mitochondrial viability and correlates with PBR expression, regeneration processes and tissue reparation.

Moreover, cold ischemia influences long-term histology and interstitial changes in the pig kidney independently from allogenicity. Vimentin staining is modulated by IRI. Atrophic tubules lacked a brush border, thickened basement membrane and were immunoreactive for vimentin, which is known to be expressed by degenerating and regenerating cells (Nakatsuji et al., *Virchows Arch.*, 433:359-67, 1998).

Furthermore, observations indicate that cellular infiltration strongly correlates with the intensity of renal damage. After implantation, renal damage was significantly reduced in kidneys preserved with UW solution for 1 h or 24 h when compared to 48 h and 72 h preservation. The data also suggest that T cells play a major role in the development of renal IRI mediated probably by adhesion of infiltrating T cells to renal tubular cells. However, a role for lymphocytes in this autotransplanted pig kidney model is not immediately intuitive based on classic immunologic paradigms. Classically, T cell activation has been thought to require foreign antigen bound to a self-major histocompatibility complex molecule together with costimulatory signals by antigen-presenting cell. The absence of foreign antigens suggests that alloantigen-independent T cell activation may be involved in renal IRI. Accordingly, the present observations are consistent with a recent study, which demonstrated that the $CD4^+$ is an important mediator of ischemic injury (Burne et al., *T. Clin. Invest.*, 108:1283-90, 2001).

PBR is known to be involved in cholesterol transport in steroidogenic organs. However, the kidney is not a steroidogenic organ. Thus, a role for PBR and cholesterol transport in IRI and its long-term effect on renal function was not obvious. However, based on the model data, it appears that PBR has a more general role in intracellular cholesterol transport, trafficking and compartmentalization. Not wishing to be bound by theory, PBR expression is implicated as a key mediator, in a second step, after up-regulation of proximal tubule cholesterol content, which contributes to stabilization of the plasma membrane. Therefore, PBR expression may be utilized as a more efficient and general marker of regeneration than other markers of chronic injury.

Consistent with an important general role for PBR, and supporting the validity of the model system, we have observed that PBR localization in human kidney is very similar to pig kidney. Furthermore, the PBR sequence presents a high sequence homology (>80%) across species. Accordingly, the pig model may be used to assess new protective drug or preservation solutions and give new insights in IRI pathophysiology, which are applicable to humans (Oke et al., *Mol. Cell Endocrinol.*, 83:1-9, 1992). Therefore, measuring PBR expression level in tissues comprises an improvement to animal model methods of transplant research such as are described in *Handbook of Animal Models in Transplantation Research* by Donald Cramer, Luis G. Podesta, Leonard Makowka, CRC Press; (1994). The molecular mechanisms that mediate this modulation of PBR remain undefined. This is a novel approach in renal transplant management and can provide new insight in the mechanisms of IRI. Since PBR is localized in the same areas in the human and pig kidneys, the improved pig model system provides a method for development of clinical strategies for the prevention of delayed graft function and improvement of renal reparation process.

In practicing such a method, clinical transplantation strategies and techniques may be efficiently assessed by measuring the course of PBR expression as a function of variation in procedural parameters or techniques. Such a method is preferably applied in the model system prior to further study in a clinical setting.

The expression level of PBR in sample tissue may be determined by any appropriate method recognized in the art. Appropriate methods which will be known and recognized in the art include, for example, immunological methods and the use of radiolabeled or fluorescent ligands of PBR to measure the level of PBR directly, such as ELISA assays, immunohistochemistry, electrophoretic blotting and molecular biology methods, such as expression profiling, to measure the cellular level of mRNA encoding PBR. The observed expression levels may be compared to values in normal tissue and/or to time course profile values from prior therapeutic experience. The invention provides that such methods may be conducted in microscale using "lab-on-a-chip" technology. In addition, it is possible to measure PBR expression levels by isotopic labeling of ligand compounds which may be observed by in vivo scanning methods such as magnetic resonance, e.g., MRI.

Immunohistochemical measurement of PBR expression is illustrated in the Examples. Another exemplary assay format which may be used to monitor the expression level of PBR is measurement of mRNA expression. For instance, mRNA expression may be monitored directly by hybridization to nucleic acids derived from the PBR sequence. Total RNA or mRNA is isolated from tissue samples by standard procedures such those disclosed in Sambrook et al., *Molecular Cloning: A Laboratory Manual*, Cold Spring Harbor Laboratory, Cold Spring Harbor, N.Y. (1989); Ausubel et al., *Current Protocols in Molecular Biology* (Greene Publishing Co., NY, 1995); Maniatis et al., *Molecular Cloning: A Laboratory Manual* (Cold Spring Harbor Laboratory, Cold Spring Harbor, N.Y., 1982); and Ausubel et al., *Short Protocols in Molecular Biology: A Compendium of Methods from Current Protocols in Molecular Biology* (1999).

Probes to detect differences in RNA expression levels between cells exposed to the agent and control cells may be prepared from the published sequence of PBR. It is preferable, but not necessary, to design probes which hybridize only with target nucleic acids under conditions of high stringency. Only highly complementary nucleic acid hybrids form under conditions of high stringency. Accordingly, the stringency of the assay conditions determines the amount of complementarity which should exist between two nucleic acid strands in order to form a hybrid. Stringency should be chosen to maximize the difference in stability between the probe:target hybrid and potential probe:non-target hybrids.

Probes may be designed from the nucleic acids of the invention through methods known in the art. For instance, the G+C content of the probe and the probe length can affect probe binding to its target sequence. Methods to optimize probe specificity are commonly available. (See for example, Sambrook et al., (1989) or Ausubel et al., (*Current Protocols in Molecular Biology*, Greene Publishing Co., NY, 1995).)

Hybridization conditions are modified using known methods, such as those described by Sambrook et al., (1989) and Ausubel et al., (1995), as suitable for each probe. Hybridization of total cellular RNA or RNA enriched for polyA RNA can be accomplished in any available format. For instance, total cellular RNA or RNA enriched for polyA RNA can be affixed to a solid support and the solid support exposed to at least one probe comprising at least one, or part of one of the sequences of the invention under conditions in which the probe will specifically hybridize. Alternatively, nucleic acid fragments complementary to PBR mRNA can be affixed to a solid support, such as a porous glass wafer. The glass or silica wafer can then be exposed to total cellular RNA or polyA RNA from a sample under conditions in which the affixed sequences will specifically hybridize. Such glass wafers and hybridization methods are widely available, for example, those disclosed by Beattie (WO 95/11755). By examining for the ability of a given probe to specifically hybridize to an RNA sample from a normal organ and a sample from a transplant organ, relative levels of PBR expression may be determined.

Microarray technology and transcriptional profiling are examples of methods which can be used to analyze the expression level of PBR in conjunction with other genes. For transcriptional profiling, mRNA from organ tissue which has undergone ischemia and reperfusion and mRNA from the same type of tissue not exposed to ischemia could be reverse transcribed and hybridized to a chip containing DNA from numerous genes, to thereby compare the expression of genes in tissue following ischemia and normal tissue. By this methodology, complementary indicators may be identified. For additional methods of transcriptional profiling and the use of microarrays, refer to, for example, U.S. Pat. No. 6,124,120.

Samples or organ tissue may be obtained during the course of a transplant procedure and post-transplant by any appropriate procedure known in the art, for example by a biopsy procedure such as by a needle biopsy.

Where PBR expression levels are observed in at least about 50% or more of tissue samples, or at least about 70% or more of tissue samples, or at least about 90% or more of tissue samples, this is taken as an indicator of organ health and may be taken as predictive of organ viability and/or a favorable outcome. Furthermore, an increased PBR expression level, preferably a substantially increased level, which may be observed by immunohistochemistry as intense PBR staining, may also be correlated with a regeneration process. Thus, where delayed graft function is observed, elevated PBR expression may indicate regeneration in the period immediately following transplantation. At later points in time, such as one week or more following transplant, PBR expression levels may provide an index of the regeneration progress. For example, an initial increase followed by a subsequent trend towards more normal expression level has been seen to track the regeneration progress. Where PBR expression levels are substantially reduced or PBR is not detected in tissue samples, this may be taken as an indicator of mitochondrial damage and/or of organ damage which may be severe, low organ viability, or as a predictor of a non-favorable outcome.

The method of the invention can be used to determine a discriminating marker in the case of non-heart beating donors, for example as a marker of organ viaility. Furthermore, the measurement of PBR expression level can be used in conjunction with other indicators of organ health and function. Preferably, the methods of the invention will be practiced as a part of the morphological study undertaken after transplantation, such as kidney transplantation. The index of organ health and recovery provided by the methods of the invention may be considered in association with other indices and immunomarkers which are used in the clinic.

The following examples of the methods of the invention as applied in an animal model system are intended to illustrate the invention and should not be construed as limiting the invention in any way.

EXAMPLES

Materials and Methods:

Surgical Procedures and Preservation Solution and Experimental Design:

An art accepted model of cold ischemia and reperfusion injury in autotransplanted pig kidney was used (Goujon et al., Kidney Int., 38:838-50, 2000; Hauet et al., J. Pharmacol. Exp. Ther., 292:54-260, 2000; Hauet et al., J. Am. Soc. Nephrol., 11:138-48, 2000). Briefly, following nephrectomy, kidneys were immediately cold-flushed and preserved at 4° C. for 24, 48 or 72 hours, after which the organs were autotransplanted. Ureteneocystostomy and contralateral nephrectomy were performed. All surgical procedures were performed aseptically. The preservation solution was the University of Wisconsin (UW) solution (Ploeg et al., Transplantation, 46:191-96, 1988). The animals were divided into six groups: control and uninephrectomized (Nef) age-matched group, (n=6, respectively), group UW1 h (UW, 1 h preservation, n=10), group UW24 h (UW, 24 h preservation, n=10), UW48 h (UW, 48 h preservation, n=10), and group UW72 h (UW, 72 h preservation, n=10).

Renal Function:

Endogenous creatinine (Cr) clearance ($C_{cr}$: ml/min), urine proteins excretion and fractional excretion of sodium ($FE_{Na}$: %) were measured before kidney preservation and on post-operative days 1, 3, 5, 7 and 14 (D1-D14) and 4 to 12 weeks after autotransplantation (W4-W12). $C_{cr}$, and $FE_{Na}$ were calculated as previously described (10). $Na^+$ level was measured by flame photometry and creatinine was measured enzymatically with an automatic analyzer (Kodak Ektachem 700 XR, Ortho, Paris, France). Twenty-four-hour protein excretion was measured after precipitation by using a colorimetric reaction with pyrogallol (Laboratoire Biorea, Talant, France).

NMR Experiments:

Damage to the renal medulla causes the release in urine of tri-methyl amine-N-oxide (TMAO), which is an osmolyte molecule synthesized in the renal medullary cells. Urine and plasma samples from control and preserved kidneys were studied as described by Hauet et al., (J. Pharmacol. Exp. Ther., 292:254-60, 2000; J. Am. Soc. Nephrol., 11:138-48, 2000). For urine NMR spectra, the ratios of TMAO to Cr were calculated and expressed in mol/mmol of Cr. To assess proximal tubular injury, the ratios alanine to Ct concentration were also determined in urine. Citrate is a citric acid cycle intermediate and its reduced excretion is associated with the impairment of oxidative metabolism and chronic metabolism acidosis. The ratio of the citrate to Cr was also measured in urine and expressed in μmol/mmol Cr.

Histology:

After 1, 24, 48 or 72 h cold storage and 40 minutes of reperfusion, at day 7, day 14 and 4 to 5, and 10 to 12 weeks after surgery, biopsy tissue samples from the deep cortex-outer medulla region were performed. Samples were fixed with Dubosq-Brasil and 10% formalin in 0.01 mmol/liter phosphate buffer (pH 7.42) and embedded in paraffin. Conventional stains were applied (hematoxylin and eosin, periodic acid-Schiff). Histological analysis concerned proximal tubular cells and particularly the brush border. Two observers who were unaware of the origin of the slides reviewed light microscopic studies. Light microscopic sections were examined for tubular necrosis, tubular dilatation, and intratubular detachment. Histological lesions were expressed in percent of kidney samples using a previously described semi-quantitative scale: 0—no abnormality; 1—mild lesions affecting less than 25% of kidney samples; 2—lesions affecting 25-50% of kidney samples; 3—lesions affecting 50-75% of kidney samples; 4—lesions affecting more than 75% of kidney samples.

Immunohistochemistry:

Tubulointerstitial injury was defined as inflammatory cell infiltrates, tubular atrophy or interstitial fibrosis. To estimate the level of tubulointerstitial fibrosis, tissue sections were also labeled with Picro Sirius for collagen identification (collagen I and III). The amount of interstitial fibrosis was determined in Picro Sirius stained sections by a semi-quantitative imaging technique. The percentage of Picro Sirius stained surface was determined on ten different tissue sections viewed at (100 magnification in each experimental condition and expressed as percent of the total surface area examined). Tubular atrophy, interstitial fibrosis and glomerulosclerosis were semi-quantitatively scored on a scale of 0 to 4+ by two pathologists blinded to the experimental conditions (0, normal; 0.5, small changes affecting 5 to 10%; 1, changes affecting 10 to 25% of specimen area; 2, changes affecting 25 to 50% of specimen area; 3, changes affecting 50 to 75% of specimen area; 4, changes affecting 75 to 100% of specimen area). Indirect immunofluorescence using a monoclonal antibody against the swine vimentin (clone V9, MCA862, Serotec Product Data Sheet, Oxford, United Kingdom) was also performed. Immunohistochemistry was performed on paraffin embedded sections. Sections were preincubated with normal goat serum for 30 minutes and incubated with primary antibody (1:40) for 30 minutes at room temperature. Sections were then incubated with the secondary antibody (rabbit anti-mouse IgG HRP conjugate). Immunolocalization of PBR was determined using an affinity purified anti-PBR peptide antiserum raised against an amino acids sequence (amino-acids 9-27, VGLTLVPPSLGGFMGAYFVR) conserved across species (Hardwick et al., Int. J. Cancer, 94:322-27, 2001; Li et al., Proc. Natl. Acad. Sci. USA, 98:1267-1272, 2001; Lacapere et al., Biochem. Biophys. Res. Commun., 284:536-41, 2001; for additional examples of methods see, Oke et al., Mol. Cell Endocrinology, 87:R1-R6, 1992; Suarez-Quian et al., Endocrinology, 132:444-58, 1993; Amri et al., Endocrinology, 137:5707-18, 1996; Hardwick et al., Canc. Res., 59:831-42, 1999). Paraffin embedded sections were incubated with rabbit anti PBR (1:400, dilution with 10% FBS-PBS) for 1 h at room temperature. After rinsing the sections in PBS, horseradish peroxidase conjugated goat anti-rabbit IgG (Transduction Laboratory, Lexington, Ky.), diluted 1:500. The intensity of immunostaining of vimentin was quantified on a 0 to 4+ scale (0=absent staining to 4+=dense). PBR staining was determined as follows: 100 tubule sections were examined for positive staining and the intensity of immunostaining was also quantified on a 0 to 4+ scale (0=absent staining to 4+=dense). To test the validity of this scoring system, two different observers both of who were unaware of the origin of the sections scored all vimentin and PBR stains independently.

Indirect immunocytochemistry was also performed using the human anti CD20 B cell marker which cross reacts with pig B cells (Dako, Copenhagen, Denmark), the mouse anti-pig CD4 (MCA1749; Serotec Product Data Sheet), the mouse anti-pig CD8 (MCA1223), and the mouse anti-pig MC1218 macrophage/monocyte and neutrophils markers (Serotec Product Data Sheet) for 30 minutes at room temperature. In all cases, the sections were rinsed in PBS and incubated with biotylated antispecies (Dako Ltd, Copenhagen, Denmark) for 20 minutes (1:100) at room temperature. As controls, omitting the primary antibodies, indirect immunofluorescence was performed. Phosphatase alkaline activity was revealed using freshly prepared Fas red substrate solution (Sigma, St Louis, Mo., USA) in Tris-buffered saline (TBS). Sections were counterstained in hematoxylin and mounted in Aquamount (Gurr, London, UK). All sections were also examined under blind conditions and photographed. The number of CD4, CD8, and MC1218-labeled cells per surface area ($10^4/\mu m^2$) was counted on five different tissue sections in each of the experimental conditions.

Statistical Analysis:

Mean values were calculated for each group (mean±SEM) and compared for statistical significance by the unpaired t test or variance analysis, and Student-Newman Keuls for multiple comparison tests. The unpaired t test was used for cellular infiltration and the Mann-Whitney U test was used for histologic data analyses and immunohistochemical data. Differences at a P value of less than 0.05 were considered to be significant.

Figure 1B:
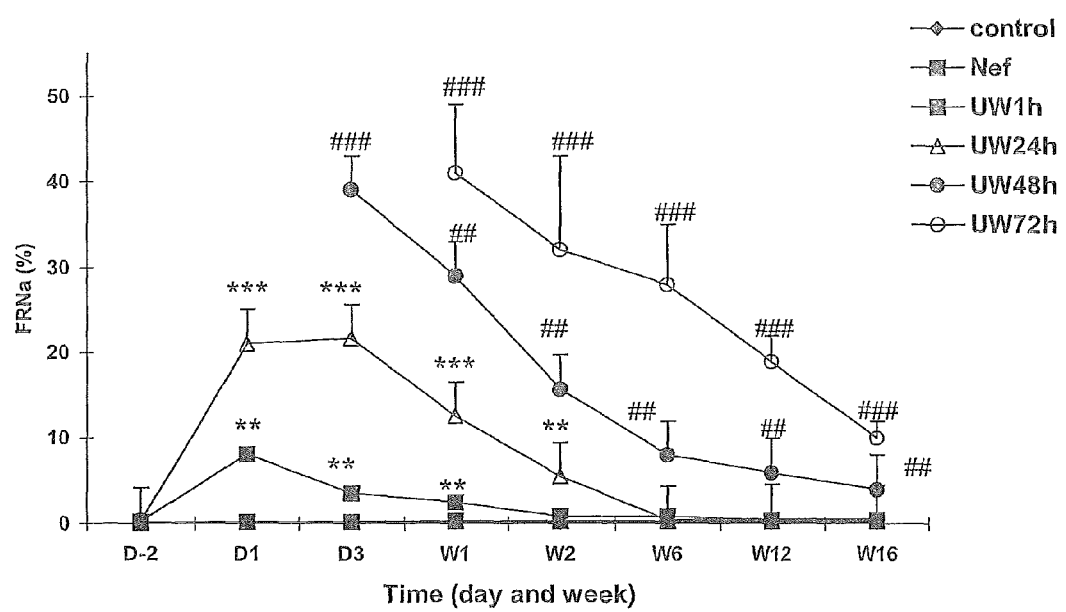
Figure 1C:
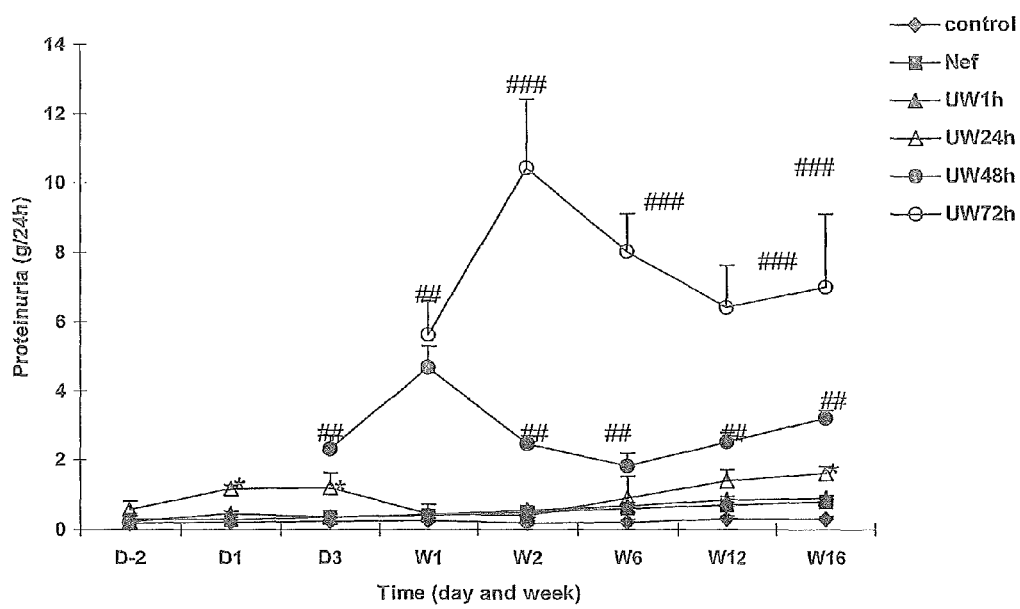
Figure 1D:
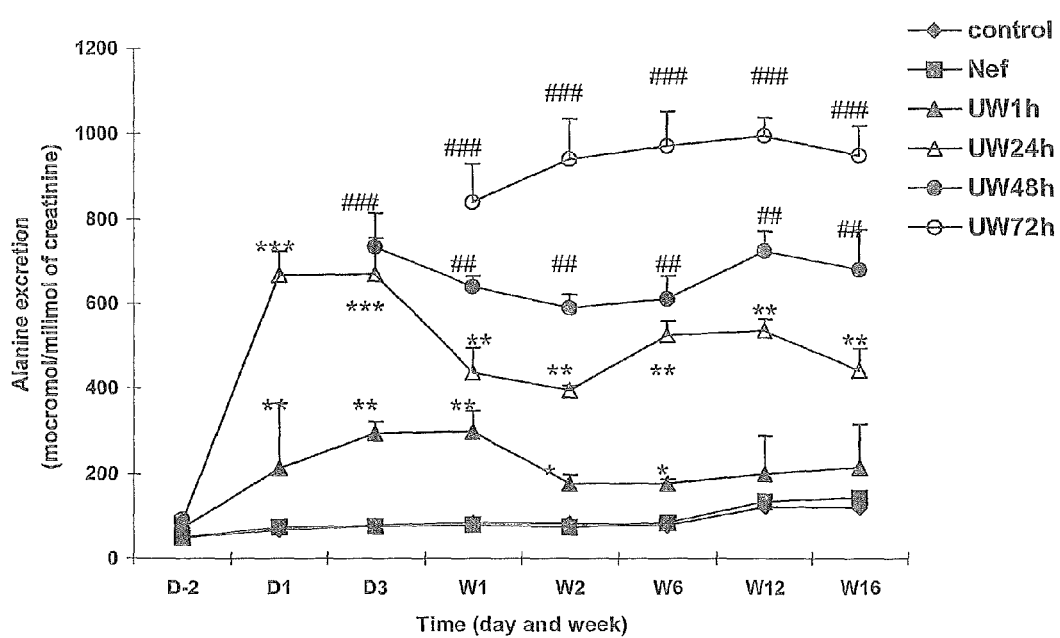

Results:

Effect of Cold Ischemia Time on Renal Function and Survival:

Total body weights and kidneys weight were not significantly different between control (43.2±2.5 kg), Nef (41.3±2.2 kg) and experimental groups (Table 1). Three pigs died on post-operative day 7 and 10 in group UW48 h and 6 pigs died on postoperative day 5 and 8 in UW72 h group. All these animals developed acute renal failure, confirmed by histological analysis. Survival was 100% in the control group, 100% in the Nef group, UW1 h group and UW24 h. Functional data were not determined in groups UW48 h and UW72 h (<100 mL/24 h from day 1 to day 5) related to a prolonged anuria before D3 and D7. As shown in FIG. 1, the cold ischemia and reperfusion affect the renal functions after autotransplantation. $C_{cr}$ was dramatically decreased in UW groups particularly after 48 h cold storage (FIG. 1A) and conversely $FE_{Na}$ was significantly higher in UW preserved kidneys (particularly in groups UW48 h and UW72 h) than in control group (FIG. 1B). The highest $C_{cr}$ occurred in experimental UW1 h after autotransplantation, between D1 and W2. There was a transient proteinuria in all-experimental groups, which decreased progressively between D1 and W4. Progressive proteinuria developed again after week 4 following surgery in urine from Nef group and kidneys preserved and transplanted particularly in groups UW48 h and UW72 h. Proteinuria was significantly lower in UW1 h groups than those cold flushed and preserved for 24, 48 and 72 h in UW solution (FIG. 1C). Aminoaciduria was significantly reduced in Nef and UW1 h when compared to kidneys preserved 24, 48 and 72 h (FIG. 1E).

Figure 2A:
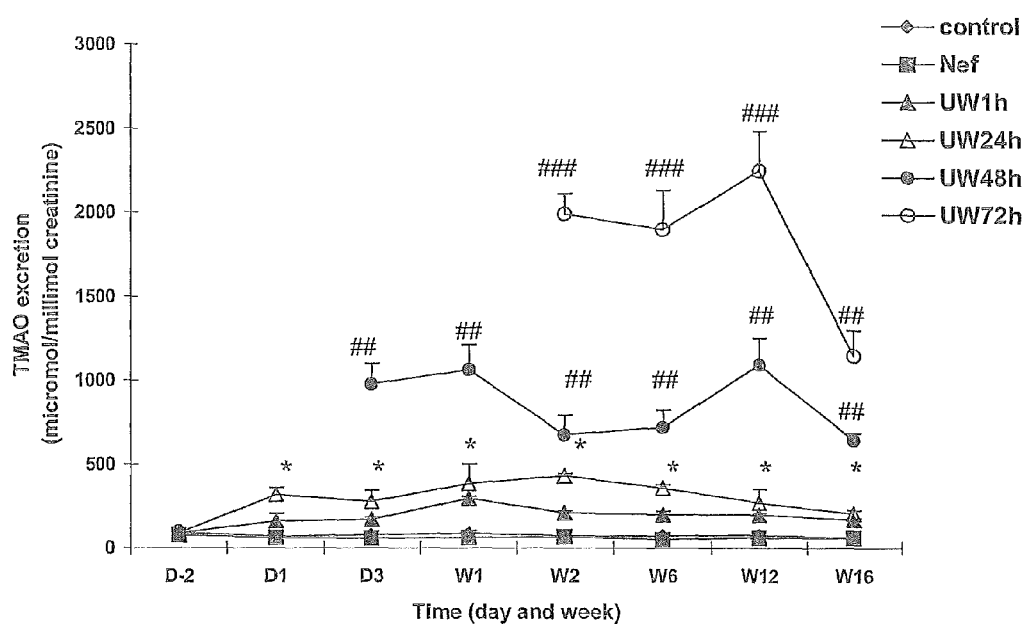
FIG. 2 shows the effect of cold ischemia on TMAO (A), and citrate excretion (B). Renal function was determined in control and uninephrectomized animals (control, closed diamond and Nef, closed square). Autotransplanted kidneys were cold-flushed and preserved with UW solution for 1 h (UW1 h, closed triangle), 24 h (UW24 h, open square), 48 h (UW48 h, open circle) and 72 h (UW72 h, closed circle). (*$P<0.05$ UW1 h and UW24 h vs. Control and Nef, $P<0.01$ UW1 h and UW24 h vs. Control and Nef, *$P<0.001$ UW1 h and UW24 h vs. Control and Nef, #$P<0.05$ UW48 h and UW72 h vs. Control and Nef, ##$P<0.01$ UW48 h and UW72 h vs. Control and Nef, ###$P<0.001$ UW48 h and UW72 h vs. Control and Nef).
Figure 2B:
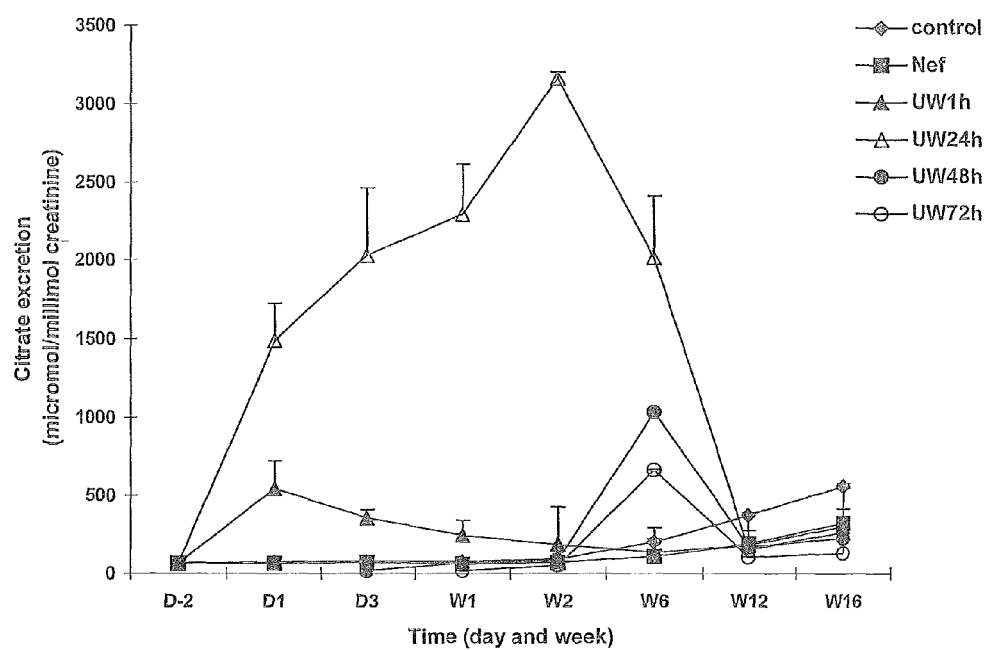

Effect of Cold Ischemia Time on Renal Medulla Injury and Citrate Excretion:

TMAO excretion was significantly reduced in UW1 h when compared to kidneys preserved for 24, 48 or 72 h (FIG. 2A). Decreased citrate excretion was detected in kidneys preserved 24, 48 and 72 h when compared to other groups between D1 and D7 (FIG. 2B). Citrate excretion remained at a low level in UW48 h, and particularly UW72 h until W4 to W6 where the excretion improved. After W12, excretion of citrate was more important in control and strongly reduced in group UW72 h.

Effect of Cold Ischemia on the Morphology of Preserved and Reperfused Kidneys:

After 40-min reperfusion, kidneys flushed and preserved for 72 h with UW solution showed significantly higher graded score than kidneys flushed and preserved with UW solution for 1, 24 and 48 h (Table 2). These differences were more pronounced with respect to tubular dilatation, intratubular cell detachment, cast formation and tubular cell brush border integrity (Table 2). Interstitial fibrosis stained with Picro Sirius were significantly reduced two weeks after transplantation in kidneys preserved in UW1 h compared with kidneys preserved 24, 48 or 72 h (Table 3). At weeks 4 and 12 following surgery, more interstitial fibrosis was observed in UW24 h, UW48 h and UW72 h groups. The mean average score for tubular atrophy, interstitial fibrosis and glomerulosclerosis was also significantly greater in kidneys cold flushed and preserved with UW for 24, 48 and 72 h than those preserved for 1 hour.

Figure 3:
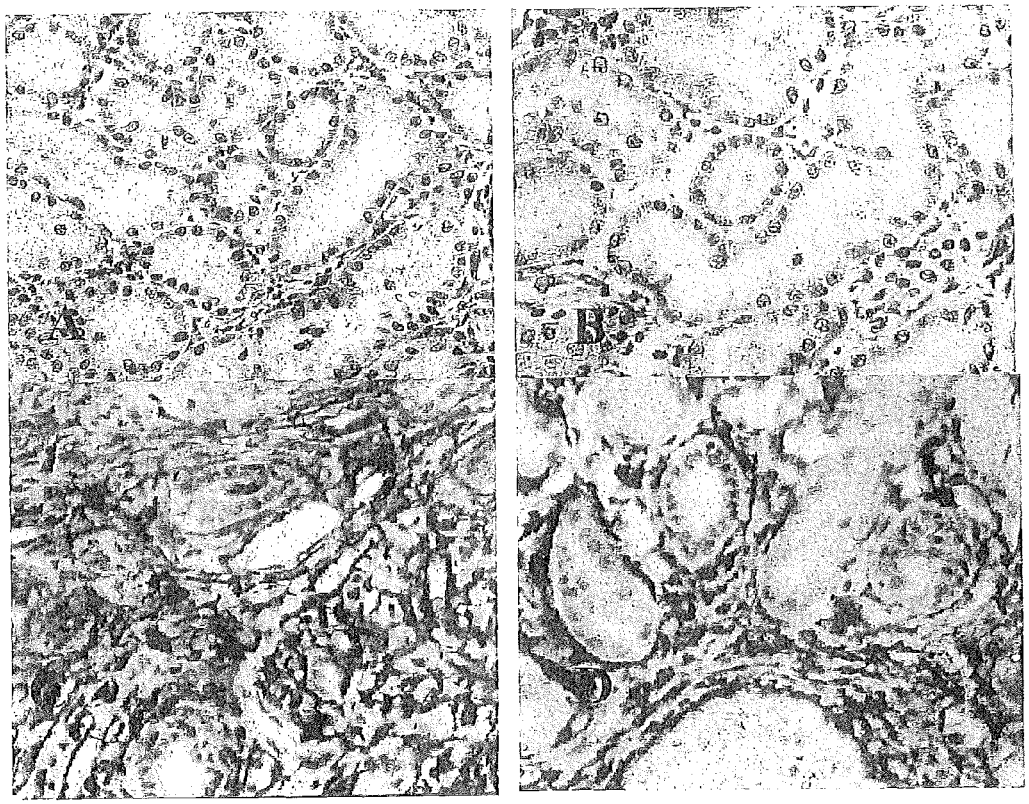
FIG. 3 shows representative interstitial immunostaining of vimentin in autotransplanted kidneys at week 16. Kidneys cold-flushed and preserved with UW solution for 1 h (A) or 24 h (B) for 48 h (D) or 72 h (C). Vimentin immunostaining was performed as described in the Examples. Original magnification: ×100.
Figure 4:
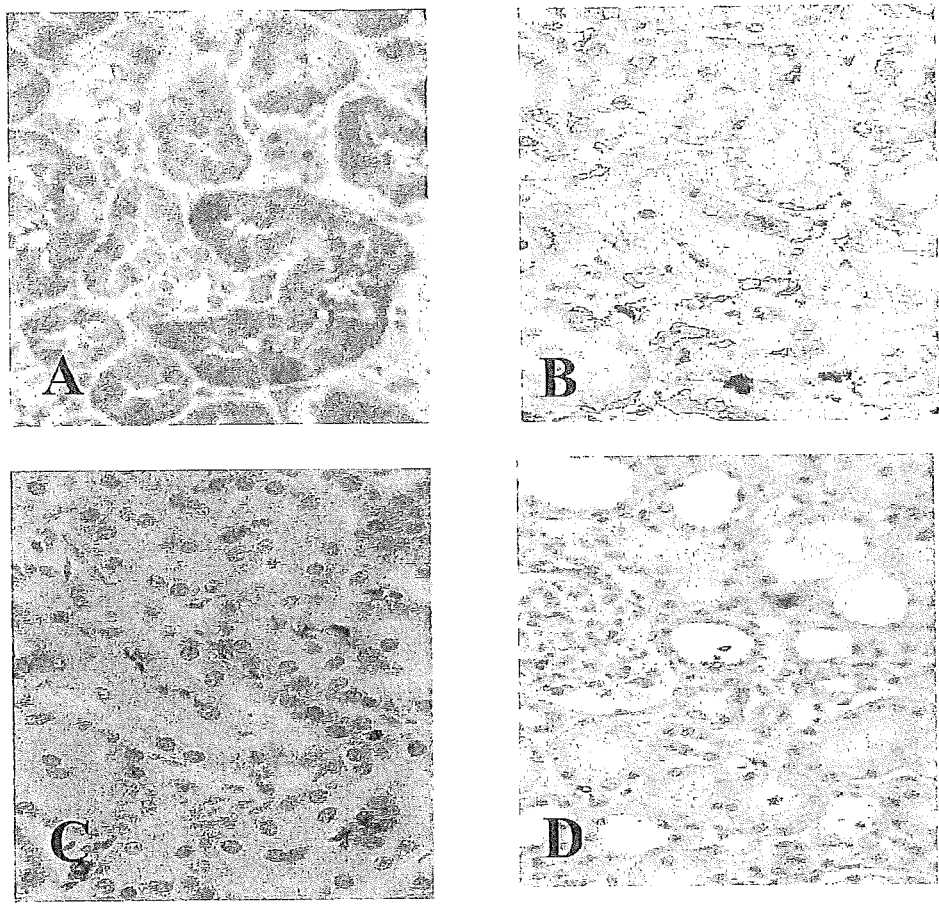
FIG. 4 shows representative immunostaining of PBR in human (A and B) and pig (C) and (D) kidneys. PBR immunostaining was performed as described in the Examples. Original magnification: ×100.
Figure 5:
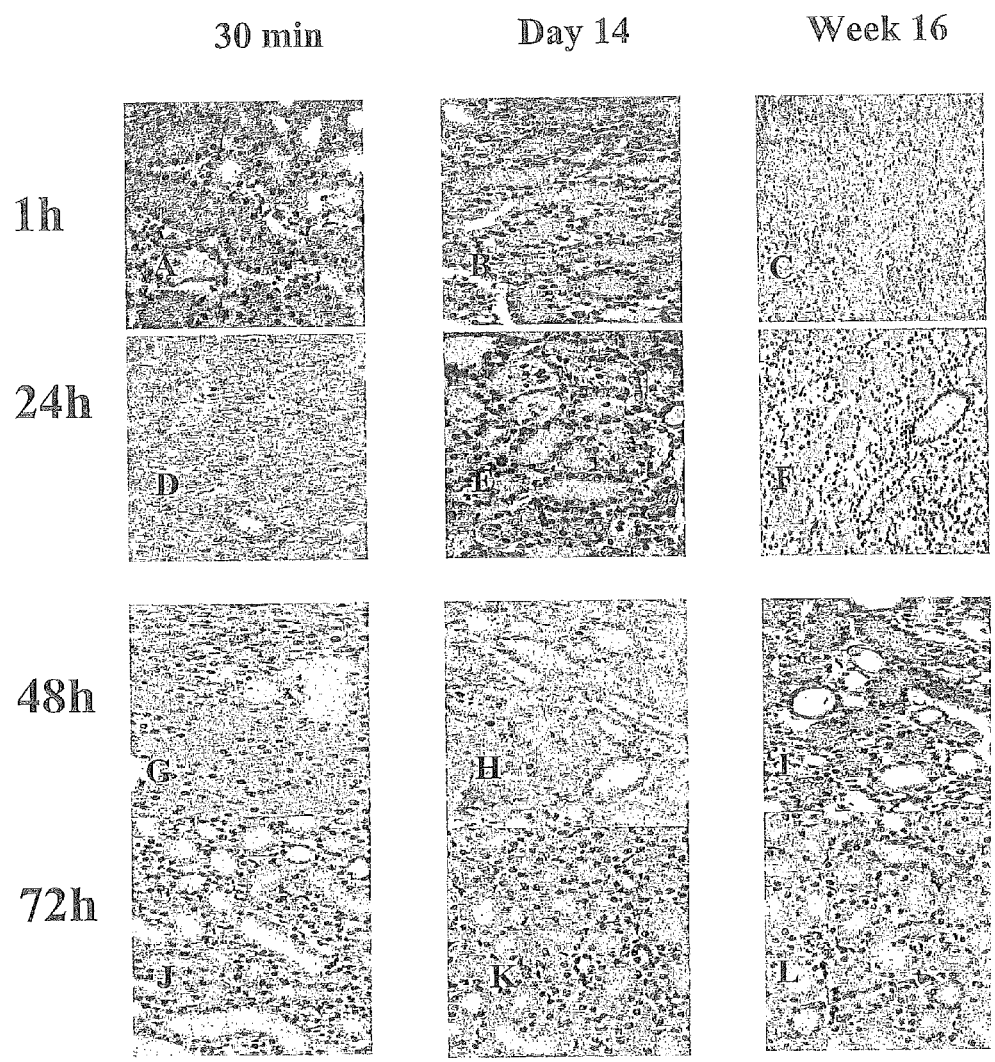
FIG. 5 shows representative immunostaining of PBR in autotransplanted pig kidneys after different times of cold preservation. Kidneys cold-flushed and preserved with UW solution for 1 h (A) after 40 to 60 min of reperfusion, (B) at week 4, (C) at week 16. Kidneys cold-flushed and preserved with UW solution for 24 h (D) after 40 to 60 min of reperfusion, (E) at week 4, (F) at week 16. Kidneys cold-flushed and preserved with UW solution for 48 h (G) after 40 to 60 min of reperfusion, (H) at week 4, (I) at week 16. Kidneys cold-flushed and preserved with UW solution for 72 h (J) after 40 to 60 min of reperfusion, (K) at week 4, (L) at week 16. PBR immunostaining was performed as described in the Examples. Original magnification: ×100.
Figure 6:
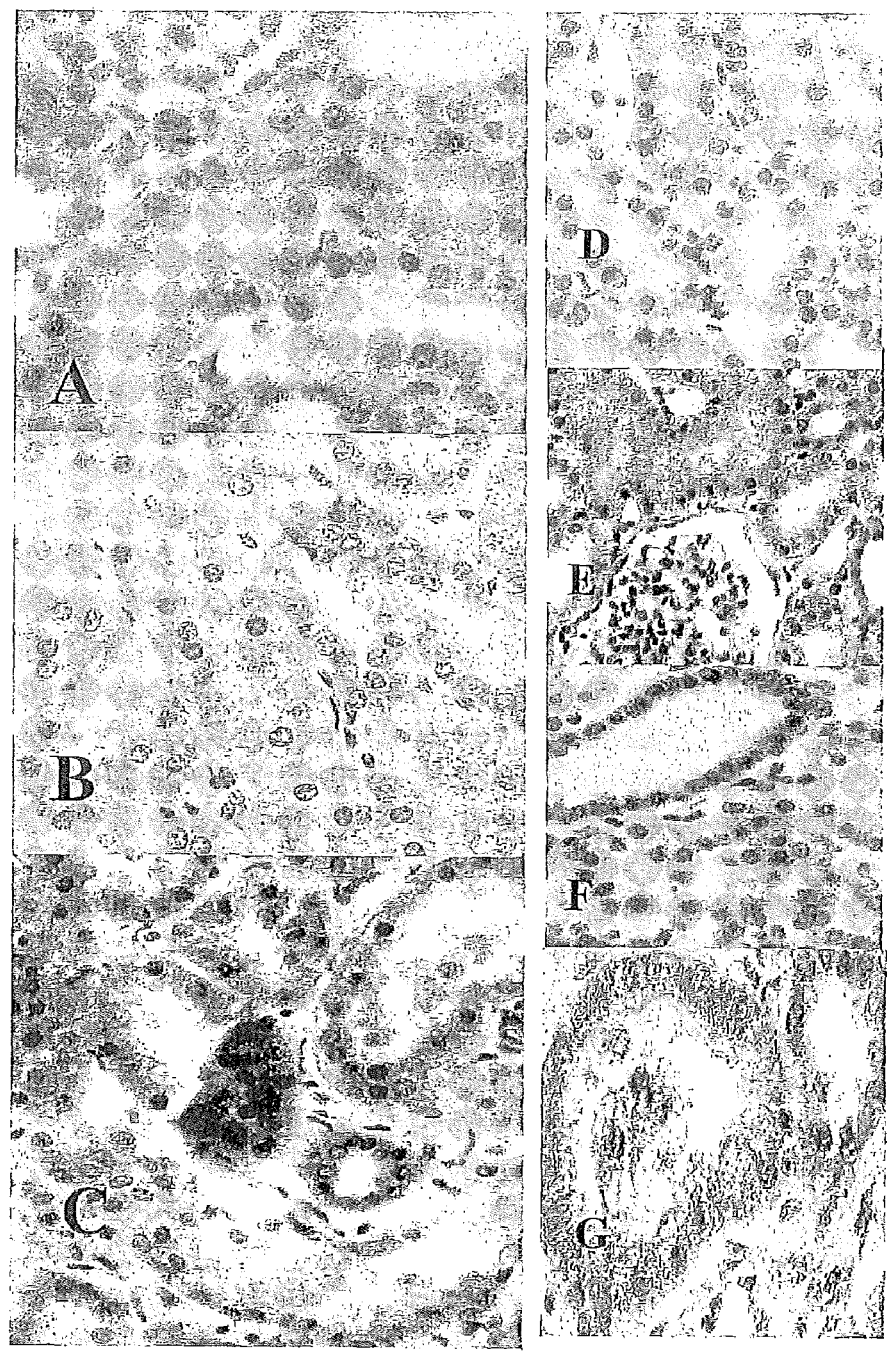
FIG. 6 shows PBR staining changes in the course of kidney regeneration. Evolution of PBR immunostaining in kidneys preserved for 1 h (A and D), 24 h (E), 48 h (B and F) or 72 h (C) and (G). PBR immunostaining was performed as described in the Examples. Original magnification: ×100.

Effect of Cold Ischemia on the Vimentine and PBR Staining:

Vimentin expression was modified by preservation conditions. The expression of vimentin was detected 4 weeks after surgery and was reduced in UW1 h and UW24 h when compared to other experimental groups. The positive reactions were localized mainly in epithelial cells lining dilated or atrophic proximal tubules (FIG. 3). In the present study, the number of vimentin-positive renal tubules increased with advancing grade of fibrosis and reduction of renal function. The immunostaining of PBR in the pig kidney is close to the immunostaining in the human kidney (FIG. 4, Table 4). The number of tubule, which expressed PBR was significantly higher in control, Nef and UW1 h groups particularly at D7, D14 and W4. The significantly strongest intensity of PBR was detected in UW1 h and UW24 h groups at D7 and D14 (FIG. 5). However the intensity was reduced after D14 in these groups when compared to UW48 h and UW72 h. As expected, PBR was also strongly expressed in regenerating tubular cells and its expression was modulated by the duration of preservation (FIGS. 6A, B, D, E and F). Atrophic tubules surrounded by interstitial fibrosis did not expressed PBR (FIGS. 6C and G). These findings were consistent with functional data.

Figure 7A:
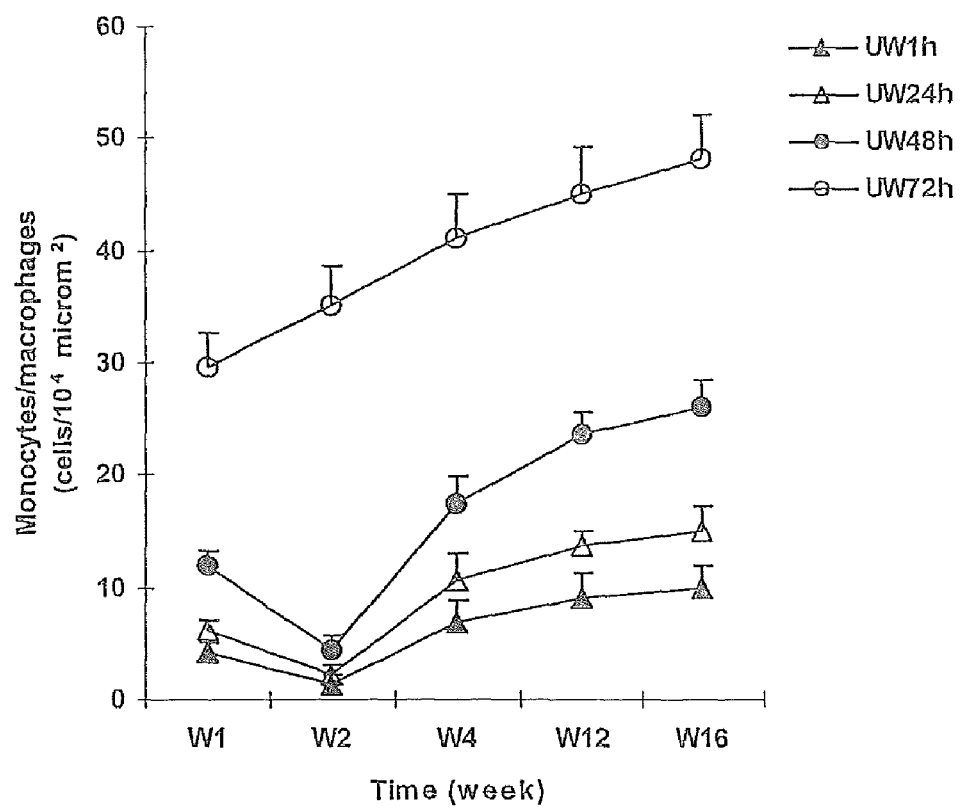
FIG. 7 shows identification of $CD4^+$ (A), $CD8^+$ (B) and $MCA1218^+$ cells (C) cells in post transplanted pig kidneys. Autotransplanted kidneys were cold-flushed and preserved with UW solution for 1 h (UW1 h, closed triangle), 24 h (UW24 h, open square), 48 h (UW48 h, open circle) and 72 h (UW72 h, closed circle). $CD4^+$, $CD8^+$ and $MCA1218^+$ cells were identified as described in the Examples.
Figure 7B:
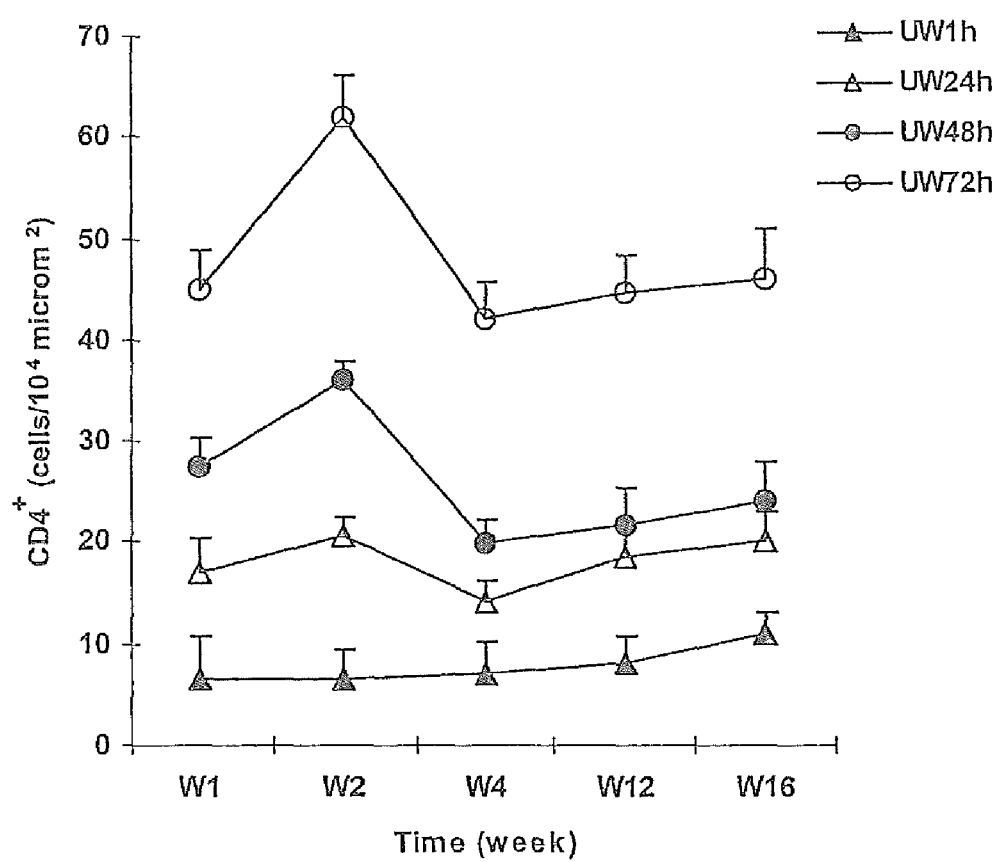
Figure 7C:
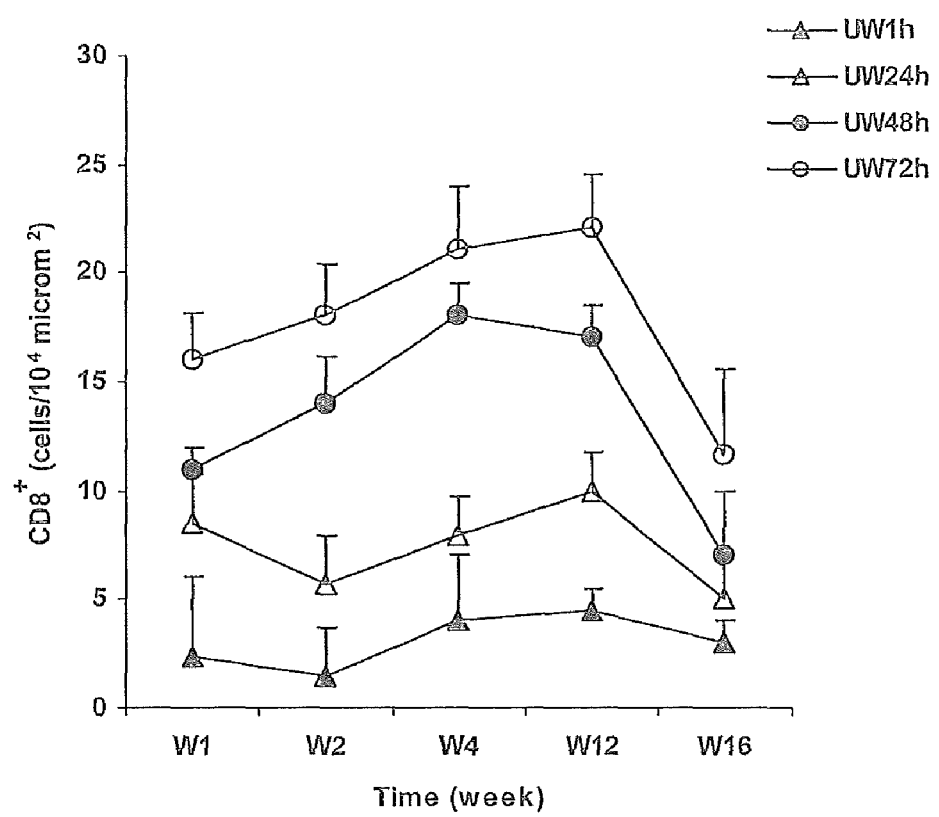

Effect of Cold Ischemia on the CD4, CD8, Monocytes and Macrophages Infiltration:

We have demonstrated in previous studies that T-lymphocytes infiltration become prominent during the early phase following autotransplantation (4,21). This study demonstrated that the preservation in UW solution for 1 h reduced the cellular infiltration in autotransplanted pig kidneys when compared to other preserved groups (FIG. 7A). As previous described, the number of CD4-positive cells gradually increased from D5 to D14, decreased from weeks 2 to 5 and gradually increased from weeks 4 to 5 to weeks 10 to 12 in the groups UW24 h and UW48 h. After 72 h cold storage, the number of $CD4^+$-cells increased from D5 to weeks 4 to 5 and from weeks 4 to 12 following surgery (FIG. 7A). A biphasic period $CD4^+$ infiltration occurred after 48 h cold storage and not after 72 h cold storage. In contrast to that observed with CD4+-cells, the number of CD8+-cells increased from D5 to weeks 2 and decreased from weeks 2 to 12 following reperfusion in 72 h cold stored kidneys (FIG. 7B). After 48 h cold storage, the number of CD8+-cells increased from week 2 to weeks 4 to 5 and slightly decreased from weeks 4 to 5 to weeks 10 to 12 following autotransplantation. Moreover, the number of CD8+-cells was also significantly reduced in UW1 h and UW24 h when compared to UW48 h and UW72 h groups. Positive staining using the anti-CD20 B cell antibody on kidney biopsies taken after reperfusion was never observed (data not shown). Positive staining with the MC1218 macrophage/monocyte was detected in all kidney biopsies taken 5 days after transplantation (FIG. 7C). However, there were more MC1218-positive cells in posttransplanted kidneys from groups UW48 h and UW72 h. This infiltration of macrophage/monocyte disappeared on biopsy samples performed two weeks after transplantation from 48 h cold-stored kidneys and decreased in 72 h cold-stored kidneys. In contrast, MC1218-positive cells were detected on biopsy samples performed 12 weeks following transplantation. The number of MCA1218-positive cells was much lower in kidneys cold flushed and preserved for 1 and 24 h in UW solution than those preserved with UW for 48 and particularly 72 h.

TABLE 1

Pigs and kidneys weight in experimental groups:

|  | UVV1h | UW24h | UW48h | UW72h |
|---|---|---|---|---|
| Pig weight (Kg) | 46.1 ± 3.1 | 48.3 ± 2.2 | 45.7 ± 4.2 | 48.1 ± 3.2 |
| Kidney weight (g) | 137 ± 7 | 139 ± 10 | 135 ± 9.7 | 136 ± 13 |

TABLE 2

Quanitation of morphological data from 48 h cold stored and normothermic perfused kidneys (Perfusion) at day 7 and 14:

| Reperfusion | UW1h | UW24h | UW48h | UW72h |
|---|---|---|---|---|
| Microvilli Desintegration | 0.5 ± 0.1 | 1.8 ± 0.1* | 3.5 ± 0.1** | 4.0 ± 0.1#** |
| Intratubular Cell Detachment | 0.5 ± 0.1 | 2.6 ± 0.1* | 3.5 ± 0.2** | 3.7 ± 0.2#** |
| Tubular Dilatation | 0.3 ± 0.2 | 2.5 ± 0.1* | 3.5 ± 0.2** | 3.8 ± 0.2#** |
| Cast Formation Day 7 | 0.5 ± 0.1 | 2.5 ± 0.1* | 3.3 ± 0.2** | 3.6 ± 0.2g#** |
| Microvilli Desintegration | 0.3 ± 0.1 | 1.2 ± 0.1* | 2.7 ± 0.1** | 3.3 ± 0.1#** |
| Intratubular Cell Detachment | 0.3 ± 0.1 | 1.1 ± 0.1* | 3.2 ± 0.2** | 3.5 ± 0.2#** |
| Tubular Dilatation | 0.3 ± 0.1 | 0.7 ± 0.1* | 3.0 ± 0.2** | 3.5 ± 0.2#** |
| Cast Formation Day 14 | 0 | 0.4 ± 0.1* | 2.5 ± 0.2** | 3.0 ± 0.2#** |
| Microvilli Desintegration | 0 | 0.6 ± 0.1 | 2.5 ± 0.2** | 2.9 ± 0.2 |
| Intratubular Cell Detachment | 0 | 0.5 ± 0.1 | 2.9 ± 0.3** | 3.2 ± 0.3 |
| Tubular Dilatation | 0 | 0.6 ± 0.1 | 2.5 ± 0.2** | 3.1 ± 0.2 |
| Cast Formation | 0 | 0 | 0.7 ± 0.2** | 1.2 ± 0.2 |

*P < 0.05 UW72h, 48 h, 24 h vs UW1h
**P < 0.01 UW72h, 48 h, 24 h vs UW1h
P < 0.05 UW72h vs UW48h
P < 0.01 UW72h vs UW48h

TABLE 3

Quantitation of tubular atrophy, interstitial fibrosis and glomerulosclerosis:

| | Week | UW1h | UW24h | UW48h | UW72h |
|---|---|---|---|---|---|
| Tubular atrophy (%) | 2 | 1.8 ± 0.4 | 5.4 ± 1* | 18.7 ± 1.7*** | 26.5 ± 3#*** |
| | 4-5 | 2.5 ± 0.5 | 8.5 ± 1.5** | 21.5 ± 2.4*** | 34.8 ± 3.4#*** |
| | 10-12 | 2.9 ± 0.6 | 10.2 ± 2** | 28.6 ± 3.2*** | 42.5 ± 4.1#*** |
| | 16 | 3.2 ± 0.6 | 11.5 ± 2.4** | 35.4 ± 3.5*** | 59.5 ± 5.2#*** |
| Interstitial fibrosis (%) | 2 | 4.2 ± 1.0 | 8.2 + 1.1* | 12.6 ± 1.7*** | 26 ± 3.0#*** |
| | 4-5 | 5.1 ± 1.8 | 11.4 ± 1.5* | 17 ± 2.4*** | 33 ± 3.8#*** |
| | 10-12 | 7.5 ± 2.2 | 16.2 ± 1.5* | 26 ± 3.2*** | 45 ± 4.6#*** |
| | 16 | 9.1 ± 3 | 21.5 ± 2.4** | 32 ± 3.5*** | 65 + 5.0#*** |
| Glomerulosclerosis (%) | 2 | 0 | 8.5 ± 3.2 | 19.8 ± 1.9 | 29.8 ± 3.4# |
| | 4-5 | 1.5 ± 0.4 | 12.5 ± 2.3** | 23.5 ± 2.9*** | 34.7 ± 4.0#*** |
| | 10-12 | 1.9 ± 0.3 | 16.3 ± 2.5** | 32.6 ± 3.2*** | 46 ± 5.0#*** |
| | 16 | 2.2 ± 0.4 | 17.9 ± 2.7** | 39.4 ± 3.5*** | 62.8 ± 4.9#*** |

*P < 0.05 UW72h, 48 h, 24 h vs UW1h
**P < 0.01 UW72h, 48 h, 24 h vs UW1h
***P < 0.01 UW72h, 48 h, 24 h vs UW1h
P < 0.05 UW72h vs UW48h

TABLE 4

Quantitation of PBR expression on tubule and intensity of PBR staining:

| | Week | UW1h | UW24h | UW48h | UW72h |
|---|---|---|---|---|---|
| PBR expression on tubule (%) | 2 | 85 ± 2.4 | 76 ± 3.4 | 36 ± 3.4 | 15 ± 21#** |
| | 4-5 | 88 ± 3.3 | 79 ± 2 | 37 ± 4.5 | 17 ± 2#** |
| | 10-12 | 90 ± 4 | 82 ± 2.2 | 40 ± 4.1 | 19 ± 3#** |
| | 16 | 94 ± 4.1 | 85 ± 3.2 | 45 ± 4.1 | 21 ± 3#** |
| Staining intensity of PBR (+) | 2 | +++/++++ | +++ | +/++ | 0/+ |
| | 4-5 | ++ | +++ | ++ | + |
| | 10-12 | ++ | +++ | ++/+++ | +/++ |
| | 16 | ++/+++ | ++ | +++ | +++/++++ |

*P < 0.05 UW72h, 48 h, 24 h vs UW1h
**P < 0.01 UW72h, 48 h, 24 h vs UW1h
P < 0.05 UW72h vs UW48h
P < 0.01 UW72h vs UW48h

REFERENCES

The following publications, as well as all others referenced in the disclosure, are incorporated herein by reference in their entirety:

1. Ojo A O, Wolfe R A, Held P J, Port F K, Schmouder R L: Delayed graft functions: risk factors and implication for renal allograft survival. Transplantation 63:968-974, 1997;
2. Molitoris B A, Hoilien C A, Dahl R, Ahnen D J, Wilson P D, Kim J: Characterization of ischemia-induced loss of polarity. J Membr Biol 106:233-242, 1998;
3. Zager R A, Johnson A, Anderson K, Wright S: Cholesterol ester accumulation: an immediate consequence of acute in vivo ischemic renal injury. Kidney Int. 59:1750-1761, 2001;
4. Zager R A, Burkhat K M, Johnson A C M, Sacks B M: Increased proximal tubular cholesterol content: implications for cell injury and "acquired cytoresistance". Kidney Int., 56:1788-1797, 1999;
5. Zager: Plasma membrane cholesterol: a critical determinant of cellular energetics and tubular resistance to attack. Kidney Int., 58:193-205, 2000;
6. Zager R A, Kahlom T F: Changes in free cholesterol: hallmarks of acute renal tubular injury and acquired cytoresistance. Am. J. Pathol. 157:1007-1016, 2000;
7. Zager R A, Andoh T, Bennett W M: Renal cholesterol accumulation: a durable response after acute and subacute renal insults. Am. J. Pathol. 159:743-752, 2001;
8. Krueger K E, Papadopoulos V: Peripheral-type benzodiazepine receptors mediate translocation of cholesterol from the outer to inner mitochondrial membranes in adrenocortical cells. J Biol Chem 265:15015-15022, 1990;
9. Tsankova V, Magistrelli A, Cantoni L, Tacconi M T: Peripheral benzodiazepine receptor ligands in rat liver mitochondria: effect on cholesterol translocation. Eur J Pharm 294: 601-607, 1995;
10. Goujon J M, Vandewalle A, Baumert H, Carretier M, Hauet T: Influence of cold-storage conditions on renal function of autotransplanted large pig kidneys. Kidney Int. 38:838-850, 2000;
11. Hauet T, Baumert H, Ben Amor I, Gibelin H, Tallineau C, Eugene M, Tillement J P, Carretier M: Pharmacological limitation of damage to renal medulla after cold storage and transplantation by trimetazidine. Pharmacol Exp Ther 292:254-260, 2000;
12. Hauet T, Goujon J M, Vandewalle A, Baumert H, Lacoste L, Tillement J P, Eugene M, Carretier M: Trimetazidine reduces renal dysfunction by limiting the cold ischemia/reperfusion injury in autotransplanted pig kidneys. J Am Soc Nephrol 11:138-148, 2000;
13. Ploeg R J, Goosens D, McAnulty J F, Southard J H, Belzer F O: Successful 72 hour cold storage of dog kidneys with UW solution. Transplantation 46:191-196, 1988;
14. Hardwick M, Rone J, Han Z, Haddad B, Papadopoulos V. Peripheral-type benzodiazepine receptor levels correlate with the ability of human breast cancer MDA-MB-231 cell line to grow in scid mice. Int J Cancer 94:322-327, 2001;
15. Li H, Yao Z, Degenhardt B, Teper G, Papadopoulos V: Cholesterol binding at the cholesterol recognition/interaction amino acid consensus (CRAC) of the peripheral-type benzodiazepine receptor and inhibition of steroidogenesis by an HIV TAT-CRAC peptide. Proc Natl Acad Sci USA 98:1267-1272, 2001;
16. Lacapere J J, Delavoie F, Li H, Peranzi G, Maccario J, Papadopoulos V, Vidic B: Structure and functional study of reconstituted benzodiazepine receptor. Biochem Biophys Res Commun 284:536-541, 2001;
17. Breton S, Brown D: Cold-induced microtubule disruption and relocalization of membrane proteins in kidney epithelial cells. J Am Soc Nephrol 9:155-166, 1998;
18. Alejandro V S J, Nelson W J, Huie P, Sibley R, Dafoe D, Kuo P, Scandling J D, Myers B D: Postischemic injury, delayed function and $Na^+/K^\circ$-ATPase distribution in the transplanted kidney. Kidney Int. 48:1308-1315, 1995;
19. Wang Z, Rabb H, Haq M, Shull G E, Soleimani M: Ischemic-reperfusion injury in the kidney: molecular basis of natriuresis. J Am Soc Nephrol 9:605-613, 1998;
20. Kwon O, Corrigan G, Myers B D, Sibley R, Scandling J D, Dafoe D, Alfrey E, Nelson W J: Sodium reabsorption and distribution of $Na+/K^\circ$-ATPase during postischemic injury to the renal allograft. Kidney Int. 55:963-975, 1999;
21. Trocha S D, Kevill C G, Mancini M C, Alexander J S: Organ preservation solutions increase endothelial permeability and promote loss of junctional proteins. Ann Surg 230:105-113, 1999;
22. Nakatsuji S, Yamate J, Sakuma A: Relationship between vimentin expressing renal tubules and interstitial fibrosis in chronic progressive nephropathy in aged rats. Virchows Arch 433:359-367, 1998;
23. Burne M J, Daniels F, El Ghandour A, Mauiyyedi S, Colvin R B, O'Donnell M P, Rabb H: Identification of the $CD4^+$ T cell as a major pathogenic factor in ischemic acute renal failure. J Clin Invest 108:1283-1290, 2001;
24. Papadopoulos V: Peripheral-type benzodiazepine/diazepam binding inhibitor receptor; biological role in steroidogenic cell function. Endocr Rev 14:222-240, 1993;
25. Anholt R R, Pedersen P L, De S E, Snyder S H: The peripheral-type benzodiazepine receptor. Localization to the mitochondrial outer membrane. J Biol Chem 261:576-583, 1986;
26. Papadopoulos V, Mukhin A G, Costa E, Krueger K E: The peripheral-type benzodiazepine receptor is functionally linked to Leydig cell steroidogenesis. J Biol Chem 265: 3772-3779, 1990;
27. Garnier M, Dimchev A B, Boujrad N, Price J M, Musto N A, Papadopoulos V: In vitro reconstitution of a functional peripherique-type benzodiazepine receptor from mouse Leydig tumor cells. Mol Pharmacol 45:201-211, 1994;
28. Papadopoulos V, Amri H, Li H, Boujrad N, Vidic B, Garnier M: Targeted disruption of the peripheral-type benzodiazepine receptor gene inhibits steroidogenesis in the R2C Leydig tumor cell line. J Biol Chem 272:32129-32135, 1997;
29. Lacor P, Gandolfo P, Tonon M-C, Brault E, Dalibert I, Schumacher M, Benavides J, Ferzaz B: Regulation of the expression of peripheral benzodiazepine receptors and their endogenous ligands during rat sciatic nerve degeneration and regeneration: a role for PBR in neurosteroidogenesis. Brain Res 815:70-80, 1999;

30. Ullian M E, Robinson C J, Evans C T B, Melnick J Z, Fitzgibbon W R: Role of citrate synthase in aldosterone-mediated sodium reabsorption. Hypertension 35:875-879, 2000;

31. Oke B O, Suarez-Quian C A, Riond J, Ferrara P, Papadopoulos V: Cell surface localization of the peripheral-type benzodiazepine receptor (PBR) in adrenal cortex. Mol Cell Endocrinol 83:1-9, 1992.

For routine practice of the protocols referenced herein, one of skill in the art is directed to the references cited in this application as well as the several *Current Protocol* guides, which are continuously updated, widely available and published by John Wiley and Sons, (New York). In the life sciences, *Current Protocols* publishes comprehensive manuals in Molecular Biology, Immunology, Human Genetics, Protein Science, Cytometry, Neuroscience, Pharmacology, Cell Biology, Toxicology, and Nucleic Acid Chemistry. Additional sources are known to one of skill in the art.

While the invention has been described in detail with reference to preferred embodiments thereof, it will be apparent to one skilled in the art that various changes can be made, and equivalents employed, without departing from the scope of the invention.

What is claimed is:

1. A method for assessing transplant therapy techniques in animals, comprising:
   A) determining an index of kidney health by measuring an expression level of peripheral-type benzodiazepine receptor in a kidney, whereby said index is determined by correlating the expression level of peripheral-type benzodiazepine receptor with an assessment of kidney health; and
   B) measuring an expression level of peripheral-type benzodiazepine receptor in a kidney transplanted or autotransplanted by a transplant therapy technique, and correlating the expression level of peripheral-type benzodiazepine receptor in the kidney with kidney health according to the index to assess the transplant therapy technique.

* * * * *